United States Patent [19]

Walsall et al.

[11] 4,428,382

[45] Jan. 31, 1984

[54] METHOD FOR IDENTIFYING THE PRESENCE OF ABNORMAL TISSUE

[75] Inventors: E. Peter T. Walsall; James R. Vincent, both of Cardiff by the Sea, Calif.

[73] Assignee: GST Laboratories, Inc., La Jolla, Calif.

[21] Appl. No.: 343,389

[22] Filed: Jan. 27, 1982

Related U.S. Application Data

[63] Continuation-in-part of Ser. No. 183,966, Sep. 3, 1980.

[51] Int. Cl.³ .............................................. A61B 5/00
[52] U.S. Cl. ..................................... 128/736; 364/414
[58] Field of Search ............................... 128/736, 1 R; 364/414–415

[56] References Cited

U.S. PATENT DOCUMENTS

| | | | |
|---|---|---|---|
| Re. 30,446 | 12/1980 | Meyers et al. | 128/736 |
| 3,280,636 | 10/1966 | Tomberg | 128/736 X |
| 3,306,282 | 2/1967 | Pierce | 128/736 |
| 3,847,139 | 11/1974 | Flam | 128/736 |
| 3,960,138 | 6/1976 | Doss et al. | 128/736 |
| 3,970,074 | 7/1976 | Mogos et al. | 128/736 |
| 4,053,951 | 10/1977 | Hudspeth et al. | 128/736 X |
| 4,055,166 | 10/1977 | Simpson et al. | 128/736 |
| 4,186,748 | 2/1980 | Schlager | 128/736 |
| 4,275,741 | 6/1981 | Edrich | 128/736 X |

OTHER PUBLICATIONS

Schwamm; "Thermography of Breast Carcinoma"; *Physikalische Medizin and Rehabilitation;* Oct. 1975.

Primary Examiner—Lee S. Cohen
Assistant Examiner—Angela D. Sykes
Attorney, Agent, or Firm—Blakely, Sokoloff, Taylor & Zafman

[57] ABSTRACT

A method for the (i) sequential acquisition of temperature measurements of predetermined parts of a living body, obtained under standardized conditions, both before and after the administration of a specific body stress; (ii) sampling such data to select the most representative data points, (iii) manipulating the selected data by identifying temperature asymmetries, and making certain correlative comparisons, among other manipulations; for the purpose of obtaining an objective indication of the probable presence and location of normal or diseased tissue; and (iv) providing a relatively simple quantitative measure of such indication.

20 Claims, 12 Drawing Figures

```
                    RIGHT                              LEFT
              REFERENCE MONITOR 159            REFERENCE MONITOR 224
                      3 2                              2 3
  Fig.2a         *    :   *                       *    :   *
              4  *    :       1                1       :       *  4
                 ---  *  ---                      ---  *  ---
              5  *    :       8                8  *    :       *  5
                      :                                :
                   *  :  *                          *  :  *
                      7 7                              7 6
  ==============================================================
```

```
  RIGHT BREAST
      -N-                                    o        ‡   <===
                                        o         ‡   F
                                   o          ‡   F
      -1-                        o‡               F
                               o    ‡             F
                                 o     ‡          F
      -2-                          o        ‡     F   <===
                                    o         ‡   F
                                     o            ‡
      -3-                             o       F ‡     <===
                                       o    F    ‡
                                        o   F  ‡
      -4-                                 F o     ‡   <===
                                          F   o   ‡
                                          F       ‡
      -5-                                 F       o ‡ <===
                                          F          ‡
                                          F        o ‡
      -6-                                 F          o ‡ <===
                                          F        o   ‡
                                          F o         ‡
      -7-                                 Fo          ‡ <===
                                       o  F ‡
                                    o      ‡ F
      -8-                        o         ‡     F
```

```
  LEFT BREAST
      -N- o    ‡                                  F
             o   ‡                                F
                o  ‡                              F
      -1-         o  ‡                            F
                     o    ‡                       F
                        o    ‡                    F
      -2-                o       ‡                F          Fig.2b
                          o      ‡                F
                           o     ‡                F
      -3-                   o    ‡               fF
                             o   ‡               fF
                              o  ‡               fF
      -4-                      o ‡                F
                               ‡ o                F
                              ‡       o           F
      -5-                    ‡         o           <===
                            ‡         o  F
                           ‡        o     F
      -6-                 ‡        o      fF      <===
                           ‡              fF
                          o ‡             fF
      -7-                o        ‡      ‡fF      <===
                        o          ‡      fF
                       o          ‡       fF
      -8-             o          ‡        fF      <===
```

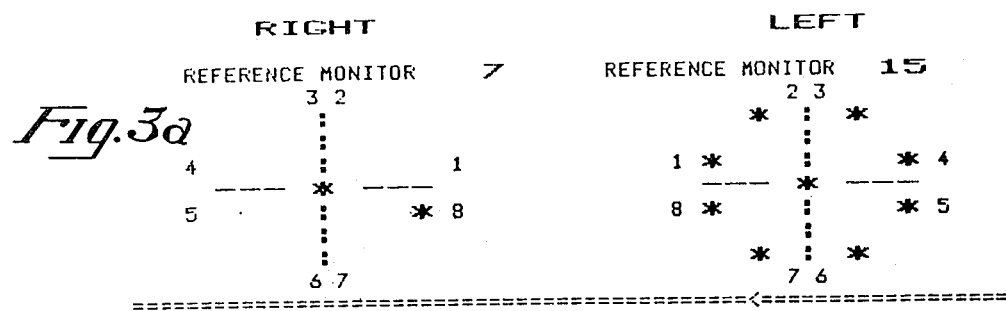

```
                        RIGHT                           LEFT
                  REFERENCE MONITOR    7          REFERENCE MONITOR    16
                        3 2                             2 3
   Fig.4a                 :                        *    :
                          :                             :
                    4 ___ : ___  1               1 ___  :  ___ * 4
                          :                             :
                    5     :    * 8               8      *       5
                          :                             :
                          :                             :
                        6 7                             7 6
         =====================================<=====================
```

```
RIGHT BREAST
   -N-     o $     f  F
           o $     f  F
            o $f  F
   -1-       of$F
             of$F
              o $
   -2-       foF$
              o $
             of$F
   -3-     o  $  F
           o  $  F
           o  $  F
   -4-     o  $  F
            o $f  F
           o $ f  F
   -5-    o $     f  F
          o $     f  F
          o $     f  F
   -6-    o $     f  F
          o $     f  F
           o $    f  F
   -7-     o $ f  F
            o $   F
              foF$
   -8-       f F o $   <===

LEFT BREAST
   -N-     o $    f  F   <===
           o $    f  F
            o $f  F
   -1-       of$F
             of$F
              o $
   -2-       foF$       <===
              o $
             of$F
   -3-     o  $  F
           o  f$F
             of $
   -4-       o  F$      <===
           o  $  F
          o $ f  F
   -5-  o $      f  F
        o $      f  F
        o $      f  F
   -6- o $       f  F
        o $      f  F
         o $     f  F
   -7-    o$  f  F
          o$  f  F
           o$f  F
   -8-     o$    F
```

Fig. 4b

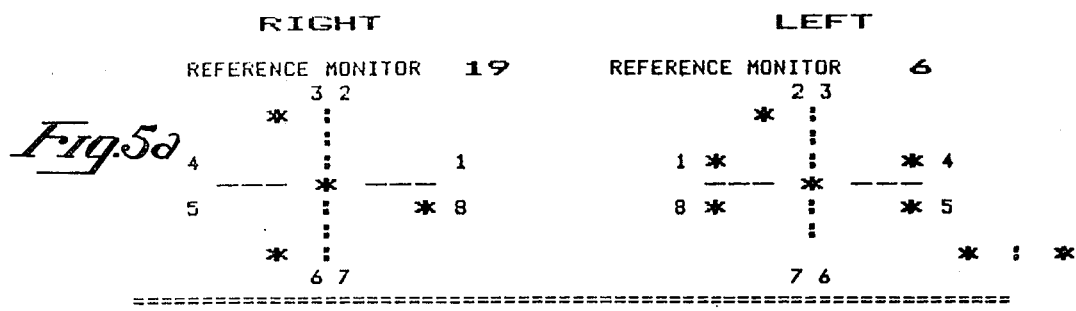

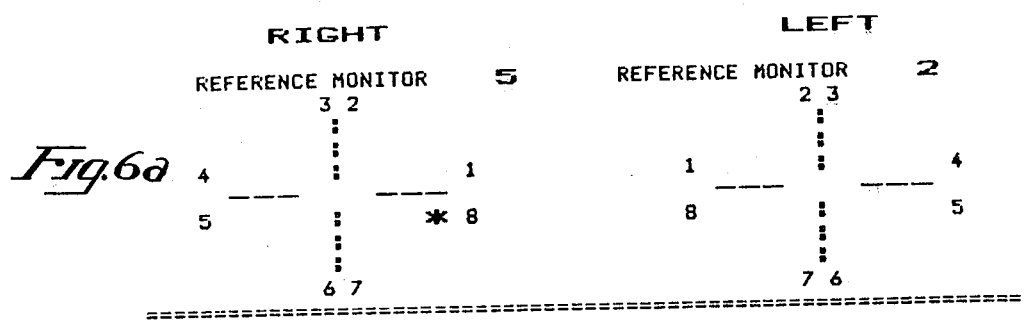

METHOD FOR IDENTIFYING THE PRESENCE OF ABNORMAL TISSUE

This is a continuation in part of applicant's co-pending application entitled "Method for Identifying the Presence of Abnormal Tissue" Ser. No. 183,966, filed on Sept. 3, 1980.

BACKGROUND OF THE INVENTION

1. Field of the Invention

The present invention relates to a method for early detection of abnormal tissue in a living body, and in particular to a method for manipulating temperature data obtained by the scanning of predetermined parts of the body so as to produce an objective indication of the probability of abnormal tissue.

2. Prior Art

Breast cancer is the most common cancer among women in the United States. Medical data based upon the size and shape of breast tumors at the time of surgery indicate that a marked improvement in the survival rate after surgery is most likely to come through early detection of the cancer; i.e., when it is small and asymptomatic. Thus, a great need has arisen for techniques and equipment that would aid in the early detection of cancerous or diseased tissue in the body. Extensive activity has been undertaken and devoted to development of methods and production of equipment useful in solving this problem. Although some of these methods and equipment may be functionally successful, actual utilization in practical clinical application has been thwarted due to health hazards, complexity, and/or the high cost of trained personnel and equipment.

At present, there are four recognized methods used in the diagnosis of breast cancer prior to biopsy. These are (i) physical examination; (ii) mammography; (iii) ultrasonography; and (iv) thermography. Mammography, which utilizes x-ray radiation, has been used extensively in the past. However, much controversy has arisen in recent years concerning excessive exposure to radiation in the detection of breast cancer. Consequently, many women now are unwilling to submit to necessary mammographic examinations which could save their lives.

Alternative techniques such as ultrasonography and thermography, which do not utilize ionizing radiation, have been developed and enhanced in recent years. Ultrasonography essentially "maps" sonar reflections and thermography "maps" infrared emissions from breast tissue respectively. In ultrasonography, the sound reflections are used to create a sonogram which can reveal alterations in the structure of normal breast tissue. Thermography is based upon the physiological observation that cancerous or otherwise diseased tissue, due to changes in vascular and metabolic activity, radiate more heat than normal, thereby elevating the temperature of the skin covering such tissue. Thus, it has been recognized that the higher skin temperature of diseased tissues can serve as a valid indicator of such a condition.

In conventional thermography, a specialized camera is used to expose a film with infrared emissions from selected surface portions of the body. The result is a thermal photograph showing temperature variations of the parts of the body scanned as bright and dark spots. Another thermographic technique known in the art is "contact" thermography, such as manufactured by Thermal Imagery, Inc., which is applied directly to the breasts and produces colored pictures. The so-called "Flexitherm" liquid crystal detection system is virtually a brassiere with cholesterol crystals that show heat changes. U.S. Pat. No. 4,055,166 to Simpson et al discloses a brassiere which includes a number of skin temperature sensors connected to battery powered integrated circuits, including storage registers for recording the sensed temperature data.

A distinct disadvantage to both ultrasonography and conventional thermography is that each depends upon a subjective analysis of the sonogram and thermogram, as the case may be, by a highly trained person. This results in reduced reliability and greater cost, making these techniques unacceptable for mass screening. The subjective nature of the analysis required by these techniques relates both to the determination of what the test results are, and to what they mean as well. For example, knowledge of the normal vascular patterns of the breast is a prerequisite to interpretation of thermograms, and there can be great variation in readings by different individuals and even in repeat interpretations of the same record by the same individual.

Schwamm of West Germany developed a system of thermography using an infrared probe (a Thermophil M202). He coupled his readings with a stress test, first using Novacaine injections or topical applications, and later substituting ice water. His rationale for such procedure is that the temperature of any part of the body is controlled by a thermal regulatory mechanism which responds to any type of body stress by vasoconstriction, with a subsequent reduction in the local temperature. The cardiovascular mechanisms which influence skin temperature of the hand, feet and other parts of the body are regulated by the sympathetic sector of the autonomic nervous sytem. Activation of the sympathetic processes results in the constriction of the blood vessels, reduction in their diameter, and a consequential decrease in peripheral circulation and skin temperature. Abnormal areas, such as those involved by cancer, do not manifest this same temperature reduction, because the blood vessels in the tumor do not constrict to the same degree as normal tissue under the same stimulation.

The present invention is an improvement on the work done by Schwamm, utilizing a direct infrared sensing device for gathering temperature data and an empirically developed methodology for manipulating such data so as to reliably detect the presence and location of diseased breast tissue.

BRIEF SUMMARY OF THE INVENTION

The method according to the present invention consists of a combination of at least two separate tests that are synergistically combined to produce an improved and highly reliable medical screen technique. This method is based on established principles of thermography and physiology. One such principle is the well established and amply supported physiological fact that the temperature of skin covering a diseased or cancerous tissue is abnormally elevated in comparison to the temperature of skin covering normal tissue. By measuring and recording the temperatures of predetermined parts of the body, and subsequently sampling and manipulating such temperature data in accordance with the teachings of this invention, it is possible to determine whether a particular part of the body exhibits a risk of having diseased tissue. The temperature measurements are taken using a commercially available temperature measuring instrument, equipped with a probe responsive to thermal radiation. The probe is passed over, but does not touch, the skin surface of the part of the body of interest to the practitioner.

A part of the body is first selected for testing. The surface of that part of the body is then imaginarily divided into a plurality of sectors. The temperature data is next obtained by scanning such imaginary sectors in a sequential scanning pattern. The temperature measurements are made after the subject's body temperature has stabilized in a temperature stabilized room (20°–23° C.). Temperature measurements of the forehead temperature are also included in the scanning sequence. The present invention uses the forehead as the temperature reference point of the body, inasmuch as it is the warmest and the most thermally stable part of the body. The use of the forehead temperature as the reference temperature reduces the number of false indications of abnormal tissue.

After the first scanning sequence in which temperature data is acquired, the body is subjected to a stress, and after a designated time interval, a second scanning sequence is conducted. Underlying the repetition of the temperature measurement sequence after stress is the earlier noted physiological fact that diseased tissue typically manifests a minimal temperature drop in response to stress.

When available, temperature scans of two identical and symmetrically, but oppositely, disposed organs may be advantageously taken. For example, the right and left breasts of a body constitute such a pair of symmetrical and oppositely disposed organs. Each breast surface may be divided, for scanning purposes, into nine sectors, the nipple being treated like a ninth sector.

After sampling the sets of temperature data measured so as to select the most representative data points, the present invention teaches the manipulation of the data in accordance with empirically derived formulations. The latter are based upon consideration of many physiological parameters developed in the course of past and present research. Among the parameters considered are (i) the degree of asymmetry of opposing identical organs; (ii) the deviation of a temperature value from its expected value; (iii) the comparative relationship of the measured temperatures to that of the reference temperature; and (iv) the temperature response of the part of the body being tested to stress.

In addition, this invention teaches methods for producing from the selected temperature data (i) a risk index score which represents a relative measure of the risk that the part of the body being tested is diseased; and (ii) a reference monitor which reflects the sujects's deviation from a standardized, physiological ideal. By comparing the reference monitor scores or periodic tests of the same patient, any major change in the physiology of the part being tested would likely be detected.

Thus, the present method is especially suited for use in the early detection of breast cancer. Because the method concentrates mainly on detecting abnormal heat patterns in the breasts, it avoids and substantially eliminates the health hazards involved in X-ray radiation, a significant disadvantage of the primary breast cancer screening method of the prior art.

The methodology disclosed is particularly suited to being implemented by a programmable microcomputer, which can provide the further capabilities of a video display to monitor the conduct of the testing and to display data, an input terminal for manual data entry, and a printer for the generation of hard copy reports.

Thus, the present invention provides a harmless, noninvasive methodology for detection of diseased tissue which (i) minimizes subjective interpretations of images and/or colors; (ii) reduces the incidences of false negative and false positive findings; (iii) yields results based upon an objective interpretation of temperature data, utilizing standardized and physiologically based criteria; and (iv) provides prompt test results in a quantitative and/or graphic form. Other significant advantages include (i) its relatively low cost; (ii) the short time required for conducting the tests, typically 15–20 minutes; (iii) the ability to conduct the tests within the normal space and environmental limitations of a doctor's office; and (iv) the fact that the tests are conducted in a dignified manner without manipulation of the breasts in any way. In view of the foregoing, the invented methodology is particularly well adapted for use in large scale screening programs aimed at the early detection of breast cancer.

Other objects and advantages of the present invention will be apparent from the detailed description thereof which follows.

BRIEF DESCRIPTION OF THE DRAWINGS

The present invention is now described in detail with reference to the accompanying drawings in which:

FIGS. 2a through 6a are breast diagrams produced by the methodology of the present invention displaying possible areas of concern with reference to the breast sectors of FIG. 1a, said diagrams relating to Case Studies 1 through 6 respectively (described below).

FIGS. 2b through 6b are temperature profiles of both breasts before and after stress with respect to the breast sectors of FIGS. 1a, indicating areas of asymmetry and the relationship of the temperature measurements shown to the forehead (i.e., reference) temperature, said profiles relating to Case Studies 1 through 6 respectively (described below).

DETAILED DESCRIPTION OF THE INVENTION

The method according to the present invention comprises three basic sequences: (1) data acquisition; (2) data sampling; and (3) data manipulation. The data being acquired, sampled and manipulated are temperature measurements of a portion of the human body; in the application to be described, the female breasts.

Data Acquisition

The basic in-office means for data acquisition is a temperature measuring instrument equipped with a hand-held temperature sensor or detector which is highly sensitive to thermal radiation. A suitable instrument, responsive to radiation in the infrared region of the spectrum, is the Thermophil M202 made by Ultrakust of West Germany. It is important that the probe enable a technician to make a gliding or scanning movement across a predetermined part of the body in a particular pattern. Further, it is preferred that the measuring instrument be adapted to automatically measure the variance in temperature between a given part of the body and a reference temperature, the instrument being pre-calibrated to the reference temperature as described below.

For the purpose of acquiring temperature data, the infrared probe and instrument should be capable of (i) measuring surface temperatures of the skin to within 0.1 degree Celsius, and (ii) responding at a sample rate of at least 20 data points per second of scan.

Figure 1A:
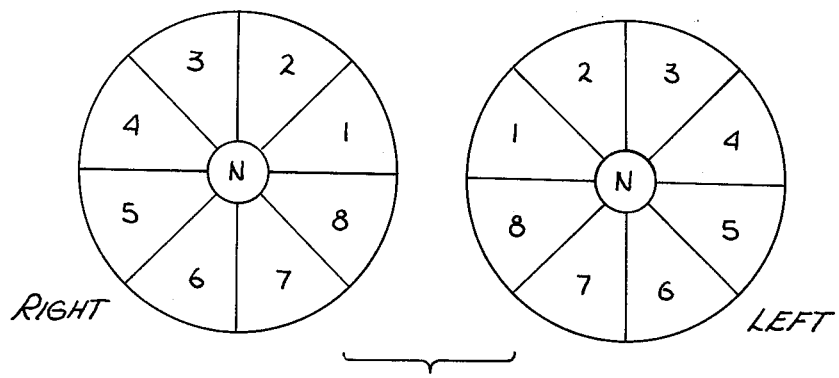
FIG. 1a is a schematic diagram illustrating female left and right breasts imaginarily divided into nine sectors each.

In adapting the present method for use in the screening of breasts for cancer, the area of each breast is divided into nine sectors, the nipple constituting a separate central sector surrounded by eight other equal radial sectors. Referring to FIG. 1a of the drawings, the left and right breasts are schematically shown, divided into the preferred nine sectors each, as described above. By visually or imaginarily dividing each breast into such small sectors, and scanning the same sequentially, it is possible to pinpoint with greater precision the exact location of any tumor or diseased tissue.

Figure 1B:
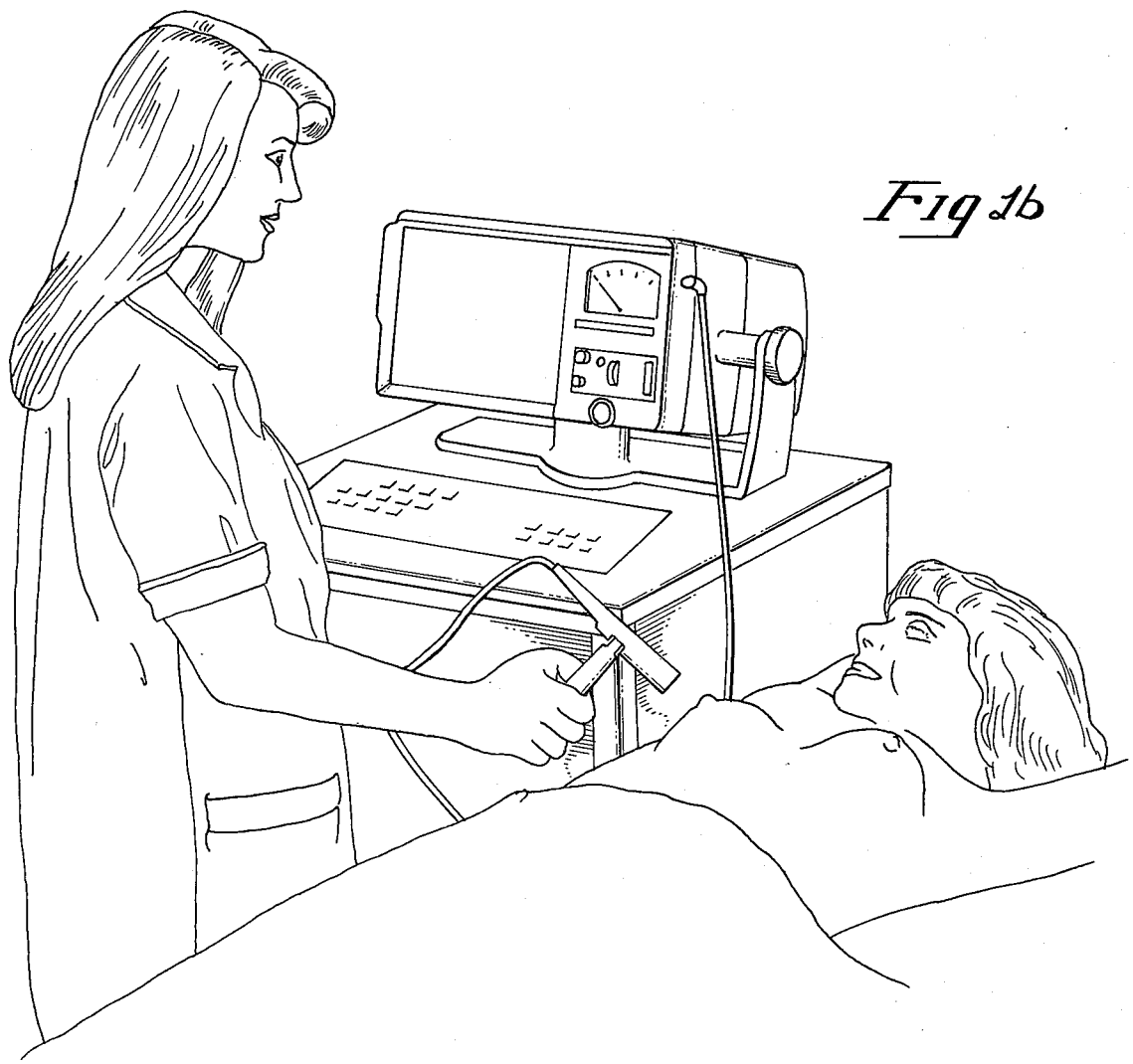
FIG. 1b is a perspective view of a technician acquiring temperature data measurements of a woman's breasts, in accordance with this invention, by sequentially scanning the sectors of FIG. 1a with a detector responsive to infrared radiation.

Prior to the acquisition of temperature data, the patient undresses to the waist in a private examining room. She is then instructed to lie in the supine position with her arms extended over her head for at least five minutes, as illustrated in FIG. 1b. This is the time necessary for the patient's body heat to become accustomed to the temperature of the room, which must be stabilized at 20°–23° C. (68°–72° F.), which has been found to yield optimum reproducability in the sequence of body temperature measurements made according to this invention. Allowing the patient's body temperature to stabilize with respect to the temperature of the room enhances the reliability of the measurements made in accordance with the teachings of the invented method.

Data acquisition is done in at least two stages. In the first stage, the temperature measuring instrument is properly calibrated. The technician then aims the hand-held, infrared probe at a wall in order to record the room temperature. Next, the probe is held perpendicularly to a point approximately 2 cm above the surface of the patient's forehead for at least five seconds. This first forehead temperature is taken to serve as a reference or individual control standard for each patient.

The present invention contemplates the use of the forehead as the preferable temperature reference point of the body. It has been discovered, through various tests and experimental investigations, that the forehead, as opposed to other parts of the body, constitutes the warmest and thermally most stable point on the body. Because the temperature of the forehead is fairly constant, it can serve as a reference point for comparing the variable temperatures of other parts of the body. By comparing the measured breast surface temperatures to such a reference temperature, the effects of a large number of medically unimportant physiological conditions which may result in elevated surface temperatures, such as, for example, those caused by superficial vascularity and hyperemia, can be effectively eliminated, thereby reducing the incidence of false indications of abnormal tissue. Another advantage in using the forehead as a reference point is that it constitutes an area of the body most accessible during an examination.

The relative temperature scale of the measuring instrument is adjusted so that the temperature of the patient's forehead, within a relative range of $-5°$ C. to $+5°$ C., has a relative value of 1.0° C. This is represented internally in a microprocessor means (described below) as 6°. Thus, if a breast surface temperature is 2° C. cooler than the forehead temperature, the former would be represented as 4.0° C. deviated on a relative Celsius temperature scale. A temperature other than 6°, such as 5° or 7°, may be used if the patient's breasts are unusually cool or warm.

Next, the "static" scan follows. With a "painting stroke" pattern, the technician uses the hand-held probe to scan the right nipple and the eight sectors of the right breast in numerical order to obtain temperature data with respect thereto, pointing the probe to the wall after each sector is scanned in order to "ground" the readings. This procedure is illustrated in FIG. 1b. The probe does not make contact with the skin, but is held approximately 2 cm above the surface. Following the acquisition of the reference temperature and the temperature data for the nipple and 8 sectors of the right breast, the above-described scanning sequence is repeated for the left breast; i.e., forehead, left nipple, the eight sectors of the left breast in numerical order. After completion of the scanning sequence for the left breast, the probe is aimed again at the forehead and held there for at least five seconds, thereby obtaining a third forehead temperature measurement. This concludes the static testing stage.

The scanning pattern used is of considerable importance in practicing the invented method. The scanning pattern preferred by the applicant involves starting at the inner portion of the sector, and working back and forth between the sides of the sector, and outwardly. Regardless of what scanning pattern is used, it is more important that the pattern be uniform and followed in every case. In the preferred scanning pattern, each sector of a breast is scanned for at least 5 seconds. Inasmuch as the preferred measurement instrument has a capability of making 20 temperature measurements per second, at least 100 temperature data points per sector are obtainable. The validation and sampling of such data points for each sector, in accordance with the teachings of this invention, are described below.

In the second stage of the data acquisition sequence, referred to as the "stress" stage, the body is subjected to a predetermined stress and allowed to achieve full physiological response to the stress. Temperature measurements of the breasts, in the above-described manner, are then repeated.

It is well known that any living body, when subjected to stress, undergoes a vaso-constrictive response that results in a temperature shift in the general range of 0.3° C.–0.5° C. The ability of the nervous system of the body to control blood flow to the skin and bring about a drop in skin temperature is a natural and spontaneous response to stress in normal tissue. Thus, the stress stage portion of the invented method is designed to minimize the false positives, which often occur with imaging thermographic measurements where normal surface vascular patterns may be misinterpreted as being an indication of disease or tissue abnormality.

The specific stress applied to the body may be physiological or psychological in nature. Physiological stress may include any of the following: Infliction of physical pain or shock to the body, administration of chemicals or drugs (for example), externally or internally to the body, and physiological cooling of the body. The latter technique constitutes self-induced body cooling, resulting from the vaso-constrictive response of the body, where the particular part to be screened is cooled indirectly by induction. Such overall cooling can be brought about by chilling the extremities of the body, as for example, the hands. Some teachings of the prior art disclose the direct cooling of the part of the body to be tested by external means being applied locally. Psychological stress would include emotional repression, inducing fear or terror or hypnotism of the subject.

It is preferable in the present method to employ physiological stress. It is quite difficult to apply and control psychological stress in a subject, under ordinary examination procedures. The test results obtained by using physiological stress appear to be more reliable than the ones using psychological stress.

Prior to stress stage data acquisition, the patient is required to place her hands, up to the wrists, in a basin of cold water with ice cubes floating in it. The wrists are to be completely covered by water for 15 seconds, in order to achieve full physiological response. The patient is then instructed to remove the hands from the water, shake them to remove excess moisture and lie on her back as before.

The stress scan temperature measurements are started at least 90 seconds after removal of the hands from the water, based upon empirical observation of when the maximum shift occurs. Typically, following the induced stress, a temperature drop of a patient's forehead of approximately 0.3° should be observed within a ten minute interval following the stress. The scanning steps followed in the static stage are then repeated for both breasts in the identical manner one more time during such ten minute interval, for the reason set forth below. Thereafter, the most representative set of data from among the two stress scans is selected for subsequent manipulation.

The methodology of the present invention, whereby both breasts are temperature scanned two times following the stress-induced reduction of body temperature is another novel feature designed to reduce the incidence of false positives. It has been observed by applicant that, due to variations in surface vascularity, among other factors, the post-stress temperature reduction characteristics of a population of healthy breasts manifest a statistically measurable variation. Thus, a healthy breast, whose vaso-constrictive response to stress is slower than normal, may appear to be a diseased or abnormal breast if a single stress scan is made too soon after subjecting the patient to stress (even if made after several minutes have elapsed and/or after apparent stabilization is achieved). However, by scanning both breasts two times after the stress-induced temperature reduction, as disclosed herein, and selecting the set of data which is most representative of a normal breast, the incidence of false positives, due to some healthy patients' slower vaso-constrictive response characteristics, is reduced.

After the stress phase tests, it is preferred that the patient complete a questionnaire which elicits information regarding medications, family history of breast cancer, any signs or symptoms related to breast masses or diseases, the presence of anxiety or menstruation. Although the information so obtained is not directly utilized in the invented method, it is of value to the physician in considering a recommendation for further workup, and in his evaluation of the test results obtained in the presence of factors, e.g., anxiety, which could affect the overall body temperature.

The preferred way of monitoring the testing process is to display the measured temperature data in digital form on a CRT or video screen. Electronic display of the temperature data, for purposes of monitoring the operation, can be readily accomplished by (i) converting the analog temperature data to digital form; (ii) storing the measured data, in digital form; (iii) selecting the most representative data; and (iv) storing the selected data in an electronic memory and displaying it on a video screen. If the technician, by checking the screen observes that any pertinent measurements are incomplete, out of sequence, unrecorded or clearly erroneous, he or she will become alerted to the non-standard performance. Upon becoming aware, prompt corrective action would be taken, whether to correct a procedural or equipment malfunction.

A suitable analog-to-digital conversion means, compatible with the analog output of a temperature measurement instrument such as the Thermophil M202 is the Data General 4223 A/D converter, although other suitable converters will be readily known to persons of ordinary skill in the electronics art.

The functions of data storage, sampling, manipulation and display are best accomplished by means of a microprocessor, such as by way of illustration, the Model MP-100 manufactured by Data General, Inc.

Data Sampling

Two stress scans of each breast are made following the static scan and the administration of a physiological stress. One set of the two sets of stress scan data is selected by taking the sum of the cooling for each breast and dividing it by two for each stress scan. The stress scan with the largest amount of cooling is the stress scan that will be utilized.

It is also necessary to obtain a single representative temperature for the forehead, and for the nipple and sectors of each breast. A 5-second scan of a breast sector typically yields at least 100 data points. Means for counting the number of data points taken between each sector scan are required. The set of data points associated with each sector scan are separated by the use of an ON-OFF switch on the sensor. The switch is depressed to the OFF position by the technician between each sector scan. If such counting means, preferably a microcomputer, determines that less than a minimum number of data points have been taken for a particular sector, e.g., at least 100, the technician would be alerted to such fact by a message displayed on the video screen which is in communication with the microcomputer. The technician would then be instructed to repeat the scan of the sector of the breast involved.

The present invention teaches the following data sampling steps for obtaining a single representative temperature, or data point, for the forehead and the nipple and eight sectors of each breast, after all of the temperature data accumulated during a scanning sequence is stored.

For each sector, nipple, and the three forehead scans, every combination of four consecutive data points are averaged together. The highest running four data point average is considered to be the representative temperature of the particular sector, nipple or forehead, as the case may be, whose data points are being sampled. This reference temperature will be referred to throughout as the "average temperature".

Other suitable data sampling techniques are known in the art, and while the above-described technique is preferred, the present invention is not limited thereto.

The foregoing sequence of data sampling steps can be implemented by a programmable microcomputer for which a suitable program can be readily designed by persons of ordinary skill in the computer art.

Data Manipulation

In order to understand the manipulations of the representative temperature data taught by this invention and disclosed hereinbelow, it is necessary to understand the objectives of the method.

The primary objective of the invented method is to assist the physician in selectively identifying those women most in need of immediate diagnostic evaluation by classifying the patient into one of three primary risk groups: one of relatively low risk of breast disease, one of intermediate risk, and the other of relatively high risk of breast disease. This latter group will be treated as a true positive. Additionally, this invention is intended to enable the physician to monitor the patient's thermal profile serially over a period of time in order to identify significant changes that may reflect physiological and/or pathological changes in the breasts.

The invented method produces a risk index score (the "GST® Index Score") and a reference monitor score for each breast (the "Reference Monitors"). The GST® Index Score, ranging from 1 to 99, ranks the patient relative to thousands of other patients whose breast temperature data serves as a data base, and provides a measure of the patient's relative risk with respect to breast cancer. The GST® Index Score represents a quantification of various physiological parameters, and therefore, indicates the degree of probability that there are abnormal tissue formations in the breasts. The GST® Index Score is divided into three basic classes as follows:

Class 1, comprising GST® Index Scores of 1–40, is where most patients in a normal population will be found. A GST® Index Score between 1–40 indicates normal or thermally inactive breast tissue;

Class 2, comprising GST® Index Scores of 41 through 80, relates to a transitional group of patients having an intermediate risk. A GST® Index Score between 41 and 80 indicates the possibility of some abnormality being present and the need for diagnostic evaluation or frequent re-evaluation.

Class 3, comprising GST® Index Scores 81–99, relates to the group with a significantly elevated probability of having diseased or abnormal tissue. A GST® Index Score of 81–99 indicates an abnormal thermal pattern, and therefore, immediate further evaluation is indicated for patients in Class 3.

It should be pointed out that a variation of a few points in the GST® Index Score is not necessarily significant because of the normal physiological changes to be expected over time. In particular, there is no exceptional significance in a GST® Index Score moving between two Classes; e.g., moving from a score of 79 to 82.

The Reference Monitor, one for the left breast and one for the right breast, is a monitoring score based upon the patient's deviation from expected breast temperature patterns. The purpose of the Reference Monitor is to provide the physician with a means of comparing his patients' scores serially over a period of time. When the thermal patterns of the breasts change substantially, as reflected by a major physiological change such as age, bust size and cup size, it should be reflected in the Reference Monitor score.

The data manipulated by the methodology of this invention comprises 42 temperature data points, 6 of which are forehead temperatures. The data are referred to by reference to the data acquisition phase in which they were obtained and the breast to which they relate. These sets of data are designated by the following letters:

$F_K$: Forehead Static Phase Scan
$B_{RK}$: Right Breast Static Phase Scan
$B_{LK}$: Left Breast Static Phase Scan
$B_{RV}$: Right Breast Stress Phase Scan
$B_{LV}$: Left Breast Stress Phase Scan The 9 temperature data points obtained during each of the above scans are the temperatures of the nipple and the eight sectors identified in FIG. 1a.

The following definitions are pertinent to the data manipulations described below:

Ipsilateral Asymmetry ("IA")

This term is defined as the deviation in the adjusted temperature of a breast sector from the expected temperature for that sector determined by standard statistical methods. A suitable set of empirically derived expected sector temperatures are shown in Table No. 1.

TABLE NO. 1

| Sector | N | 1 | 2 | 3 | 4 | 5 | 6 | 7 | 8 |
|---|---|---|---|---|---|---|---|---|---|
| Breast Right | 3.9 | 4.8 | 4.9 | 4.6 | 4.3 | 4.2 | 4.4 | 4.8 | 4.8° C. |
| Breast Left | 3.9 | 5.0 | 4.8 | 4.6 | 4.4 | 4.4 | 4.6 | 4.8 | 4.9° C. |

Corrected Contralateral Asymmetry ("Corrected CAS")

This term is defined as the difference between the average temperature of one sector and the corresponding average temperature of its mirror image counterpart sector of the opposite breast corrected for expected temperature deviations based on statistical averages attributable to cup size differential and difference in blood flow due to cardiac proximity.

Forehead Asymmetry ("FA")

This term is defined as the difference between the average forehead temperature and the average breast temperature for the right breast plus the difference between the average forehead temperature and the average breast temperature for the left breast. Thus, there will be one FA for each scan. (It is of interest to note that hyperthermias more than 1.4° C. below the extrapolated forehead values for that scan are considered at lower risk than those nearer the forehead value. Preliminary analysis of information accumulated by the applicant suggests that a local hyperthermia with a temperature of more than 1.4° C. below the forehead value, is generally due to superficial vascularity.)

Average Breast Temperature ("BA")

The average breast temperature for each set of data is defined as the simple arithmetic average of the 8 sector average temperatures (excluding the average temperature of the nipple) comprising each breast scan. Thus, $$BA(\text{Set}) = \frac{\text{Sum of the 8 average temperatures (1,2,\ldots 8) of Set}}{8}, \quad (3)$$

where the Set is RK, LK, RV, LV.

Worst Breast Average Asymmetry ("WBAA")

This term is defined as the absolute value of the greater of the following two differences:

BA(RK)−BA(LK), and

BA(RV)−BA(LV)

Worst Contralateral Asymmetry ("WCAS")

This term is defined as the maximum CAS measured with respect to all sectors in a given set of stress data (i.e., RV, LV).

Nipple Rank ("NR")

The "Nipple Rank" is computed by determining the number of sectors for each breast whose average temperature is less than the nipple average temperature during the stress scan and then taking the absolute value of the difference between these two numbers for each breast.

Minimum Cooling ("MINC")

For all sectors, the amount of cooling which occurs as a result of the stress is determined using the formula:

Static Scan−Stress Scan (per Sector)=Cooling

MINC is the lowest value of the derived "Cooling" which represents the minimum amount of cooling of any of the sectors due to the stress.

Maximum Cooling ("MAXC")

For all sectors, the amount of cooling which takes place across the stress scan is determined using the aforementioned formula. MAXC is the highest value of the derived "Cooling" which represents the maximum amount of cooling of any of the sectors due to the stress.

Forehead to Breast Differential Sector Asymmetries ("FBSA")

During each stress scan, the number of sectors whose temperature is greater than or equal to the average forehead temperature are determined for each breast.

The FBSA is the maximum of these two numbers generated for each breast.

Forehead to Breast Differential Sector Asymmetries ("FDSA")

During each stress scan, the number of sectors whose average temperature is greater than or equal to the average forehead temperature are determined for each breast.

The FDSA is the difference between the numbers.

Curve Correlation Values

The curve correlation values are determined by performing a correlation between the patient's curves and a set of standard curves. The standard curves are prepared by taking a set of temperature values for representative static and stress curves for both left and right, then correcting them with an amplitude factor based upon the patient's age group, bust size and cup size.

Areas of Concern Marking

Areas of concern are marked with an asterisk (*) on the breast sector diagram and by an arrow (⇐==) on the plotted breast temperatures. No marks are made on either breast if the patient has reported having had a mastectomy. The nipple and sectors 1-8 are marked by different means.

(1) Neither the nipple nor any sectors are marked if the average stress breast temperatures for the given side are more than 1.5° below the average forehead temperature for the stress scan.

(2) The nipple is marked if on the given side there are more than four sectors cooler than the nipple.

(3) A breast sector is marked if:

(a) It has an ipsilateral asymmetry greater than 0. The ipsilateral asymmetry is calculated from the standard curves generated for the correlation values. A generated standard curve is shifted by the normalization value for a given side, then the ipsilateral value is the difference between this standard curve sector temperature and that for the patient.

(2) The corrected contralateral asymmetry is greater than 0.5°. Note that this value is signed, i.e., the marked side must be warmer than the opposite side.

Reference Monitors

A reference monitor value is calculated for each non-mastectomy breast (mastectomy sites are assigned 0). The value is determined from the static and stress correlations, adjusted such that a perfect correlation of +1 gives a monitor value of 0, and a correlation of −1 gives 200.

GST Index Score

The index score is a number from 1 to 99 which indicates the degree of risk for atypical tissue in a patient's breast. The index is calculated from some 9 different physiological factors which are listed below:

(0) CORR—right/left stress scan correlations (1) FREL

This parameter is the relationship between the average static breast temperatures, and the average forehead temperature. It is calculated by subtracting the average right static temperatures (less nipple as in all calculations.) from the average forehead temperature, then adding this to the difference between the average left static temperatures and average forehead temperature. The resulting value is then corrected for cup size by subtracting a constant value depending on the cup size.

(2) WBAA

Breast Average Asymmetry is the largest absolute difference between the right and left breast averages for each scan.

(3) WCAS

This is the greatest corrected contralateral asymmetry for both scan and the eight breast sectors.

(4) FBSA

The greatest absolute difference between right and left breasts in the number of sectors which equal or exceed the average forehead temperature. This is done for the stress scan only.

(5) FDSA

The maximum number of sectors which equal or exceed the average forehead temperature, calculated between the stress right and left scans.

(6) NR

The greatest absolute difference between right and left Nipple Rank in the stress scan, where Nipple Rank is the number of sectors with breast temperatures less than that of the nipple.

(7) MAXC

The largest difference between static and stress breast temperatures for any sector or side. The result is corrected by subtracting a constant for the patient's breast cup size. The sign convention is 'static-stress'. Note that this is opposite to the report display convention.

(8) MINC

The smallest difference between static and stress breast temperatures for any sector or side.

The final CST Index Score is then calculated by first generating a base score from CORR and FREL. The base score is then subject to both positive and negative corrections based on the other seven parameters. If the score is less than 1 it is reported as 1, if greater than 80 then the result is compressed according to a logarithmic scheme, the maximum value being set at 99. If a patient has had a mastectomy, no score is reported. Instead the score value is set to $-1$, and the words 'MASTECTOMY PATIENT' are displayed on the reports.

Applicant has studied breast temperature data experimentally obtained from numerous women, and manipulated the data in accordance with the teachings of this invention. Further, the results of the invented methodology are correlated with physicians' reports of follow-up evaluations of selected patients (by mammography and/or biopsy). Applicant has discovered that the following characteristics, when found in total combination, appear to indicate a high risk of breast disease (not necessarily listed in their order of importance):

1. Average temperature of the breast sector is 1.0° C. or more greater than the contralateral breast sector's average temperature.
2. Average temperature of the breast is greater than the average forehead temperature.
3. Contralateral asymmetry is greater than 1.0° C.
4. The nipple is not the coldest temperature in the breast.

Applicant has discovered that the following characteristics, when present in total combination, appear to indicate a low risk of breast disease (not necessarily listed in their order of importance):

1. Both breast thermal profiles are normally shaped.
2. Both breast thermal profiles are very similar.
3. Average temperature of both breasts are within 0.4° C. of one another.
4. Average temperatures of both breasts are less than the forehead by 1.0° C.
5. Contralateral asymmetry is less than 0.6° C.
6. All sectors cool equally ($+0.2°$ C.).
7. The forehead cools.
8. The nipple is the coldest temperature of both breasts.

The data manipulations according to the teachings of this invention, like the data sampling steps earlier disclosed, can be carried out very effectively and at a high speed by a programmable microcomputer. As indicated above, Model MP-100 manufactured by Data General, Inc. has been found to be highly suited for such purpose. Moreover, such a microcomputer, when coupled to a printer, enables the printout of a hard copy report showing the GST® Index, the Reference Monitors and other information derived from the invented data manipulations, all of which is pertinent to the examining physician in screening his female patients for possible breast cancer. One possible report format is shown in FIGS. 2 through 6 and in Tables 2-6 below.

Those of ordinary skill in the computer art will be able readily to select suitable computers and to write programs therefor based upon the teachings disclosed herein. This invention does not lie in the particular means by which practitioners elect to practice the invented method, but in the methodology itself.

With reference to FIGS. 2 through 6, the following case studies utilizing the invented methodology are reported.

In order to enhance one's understanding of the results reported, the following notations are made with respect to the tabulations of data reported in respect to each case study (tables 2 through 6 below):

1. The forehead average temperatures are reported under the heading "Forehead values".
2. The values of the right breast and the left breast are adjusted to reflect the reference temperature (forehead) drift and are listed in the sequence in which they were measured.
3. The first mean value represents the average value of the entire right breast not including the nipple, and the second value represents the average of the breast temperatures of the left breast not including the nipple.
4. All values are recorded in degrees Celsius, but relate to an absolute scale based upon the forehead value for the individual patient. As indicated earlier, the relative temperature scale of the measuring instrument is adjusted so that the temperature of the patient's forehead, within a relative range of $-5°$ to $+5°$, has a relative value of 1.0°. This is represented internally in said microcomputer as 6°. Thus, if a breast surface temperature is 2° C. cooler than the forehead temperature, the former would be represented as 4.0° C. A temperature other than 6°, such as 5° or 7°, may be used if the patient's breasts are unusually cool or warm.
5. The tabulation under the heading "Stress Shift" reflects the degree to which each sector has cooled. The figures below the dotted line report the average of the values directly above them.
6. Under "Stress Readings," the average temperatures derived from the stress scans are reported. The average temperature values of each sector are reported for the right breast and the left breast, as is the Contralateral Asymmetry (CAS) between them.
7. The breast diagrams depicted in FIGS. 2a-6a are designed to display possible areas of concern. The sector number is indicated to facilitate the identification and correlation of the areas marked with the actual values noted in the corresponding Tables. These areas may be benign processes, cysts, cancer, congenital hyperthermias caused by vascularity, or a lack of subcutaneous fat, et al. The suspicious areas may or may not exactly match the suspicious areas indicated by mammography or sonography because of a difference in positioning of the patient.

The diagrams depicted in FIGS. 2b-6b each represent a graphic expression of the average temperatures gathered during the scans and is helpful when comparing the profiles. The actual digitized values are reported in the corresponding Tables. These figures are designed to be turned horizontally for ease of reading. The forehead average temperatures gathered during the static phase scan are represented by capital F's across the page. The forehead average temperatures gathered during the stress phase scan are presented as a series of lower case f's across the page. Usually, static forehead temperatures are higher than the stress forehead temperatures. The right breast average temperatures are presented on the first half of the graph, followed by the same profile of the left breast. The temperatures gathered during the static scan are presented by #'s and the temperatures gathered during the stress scan are presented by the o's. Usually, the #'s will be above the o's. Generally, in the normal patient's profile, the #'s and o's are all well below the forehead temperatures, and the right and left profiles will match each other in a shape which closely approximates a composite "normal" profile. The high risk patient will generally have thermal profiles that are not symmetrical. An arrow symbol signifies an area of concern.

It should be understood that the Tables and figures referred to are only one way in which the results of the data manipulations disclosed by the present invention may be displayed or printed out. Other suitable formats of data, tabulations and graphic depictions will be readily apparent to those in the field, and are matters of mere design choice. The object of any such display of data is to communicate information as efficiently and clearly as possible.

CASE STUDY NO. 1

Malignancy, Right Breast

A palpable mass was discovered upon a routine annual examination. The family history is one of breast cancer.

With reference to FIGS. 2a and 2b, the following results are noted:

TABLE NO. 2

RISK INDEX SCORE: 95

| Static Readings Forehead Values: | | | Stress Readings Forehead Values: | | | | |
|---|---|---|---|---|---|---|---|
| 5.0 | 5.1 | 5.4 | 5.0 | 5.1 | | 5.3 | |
| | | | Cooling | | | | |
| Right | CAS | Left | Right | Left | | Right | CAS | Left |

| | Right | CAS | Left | Right | Left | | Right | CAS | Left |
|---|---|---|---|---|---|---|---|---|---|
| N | 5.5 | 4.0 | 1.5 | −.6 | −.4 | N | 4.9 | 3.8 | 1.1 |
| 1 | 3.4 | 1.0 | 2.6 | .0 | −.1 | 1 | 3.4 | 1.1 | 2.4 |
| 2 | 4.3 | 1.1 | 3.2 | −.3 | −1.2 | 2 | 4.0 | 2.2 | 2.0 |
| 3 | 5.1 | 1.6 | 3.3 | −.6 | −.5 | 3 | 4.5 | 1.5 | 2.8 |
| 4 | 5.6 | 2.0 | 3.4 | −.4 | −.2 | 4 | 5.1 | 1.7 | 3.2 |
| 5 | 6.3 | 1.7 | 4.4 | −.5 | .9 | 5 | 5.8 | .2 | 5.3 |
| 6 | 6.3 | 1.7 | 4.4 | −.2 | .4 | 6 | 6.1 | 1.0 | 4.8 |
| 7 | 5.6 | .3 | 5.2 | −.5 | −.9 | 7 | 5.1 | .7 | 4.4 |
| 8 | 4.3 | .1 | 4.3 | −.4 | −.6 | 8 | 3.9 | .3 | 3.7 |
| Mean | 5.1 | | 3.8 | −.4 | −.3 | | 4.7 | | 3.6 |

AREAS OF CONCERN ARE INDICATED BELOW
GST INDEX SCORE 95

RIGHT REFERENCE MONITOR: 187    LEFT REFERENCE MONITOR: 149

```
        3       2              2       3
        I                              I
        I                              I
        I                              I
4  *            1   1                          4
- - -    - -        - - -             - - -
5                   8   8                      5
        I                              I
        I                              I
      * I   *                          I
        6       7              7       6
```

Note that:
1. Breast averages differ by 1.8° C.
2. Neither profile is normal.
3. The profiles do not match.
4. Right breast average is elevated above forehead temperature.
5. Right nipple is not the coldest.
6. Clustered hyperthermias (R4, 5, 6, 7).
7. Right contralateral hyperthermias are also iplilateral hyperthermias. Additional areas of concern in left breast #5 and #6 are due to different cooling and ipsilateral hyperthermia.

CASE STUDY NO. 2

Malignancy, Left Breast

A physician discovered a palpable mass in the outer aspect of the left breast.

With reference to FIGS. 3a and 3b, the following results

TABLE NO. 3

RISK INDEX SCORE: 86

| Static Readings Forehead Values: | | | Stress Readings Forehead Values: | | |
|---|---|---|---|---|---|
| 4.8 | 4.7 | 5.0 | 3.9 | | 3.9 | 3.7 |
| | | | Cooling | | | |

| | Right | CAS | Left | Right | Left | | Right | CAS | Left |
|---|---|---|---|---|---|---|---|---|---|
| N | 2.4 | 3.4 | 5.8 | .6 | −3.2 | N | 3.0 | .4 | 2.6 |
| 1 | 3.2 | 2.3 | 5.6 | .1 | −2.0 | 1 | 3.3 | .1 | 3.6 |
| 2 | 3.7 | 1.5 | 5.1 | −.7 | −1.6 | 2 | 2.9 | .6 | 3.5 |
| 3 | 3.1 | 1.7 | 4.8 | −.3 | −1.6 | 3 | 2.8 | .4 | 3.2 |
| 4 | 2.6 | 2.9 | 5.2 | .2 | −2.2 | 4 | 2.7 | .6 | 3.1 |
| 5 | 2.5 | 2.7 | 5.1 | .2 | −2.6 | 5 | 2.7 | .0 | 2.5 |
| 6 | 2.7 | 2.2 | 4.8 | −.1 | −2.1 | 6 | 2.8 | .2 | 2.8 |
| 7 | 2.7 | 2.8 | 5.4 | .9 | −2.5 | 7 | 3.6 | .6 | 2.9 |
| 8 | 2.4 | 3.2 | 5.7 | 1.3 | −2.5 | 8 | 3.7 | .6 | 3.2 |
| Mean | 2.9 | | 5.2 | .2 | −2.1 | | 3.1 | | 3.1 |

AREA OF CONCERN ARE INDICATED BELOW
GST INDEX SCORE 86

RIGHT REFERENCE MONITOR: 187    LEFT REFERENCE MONITOR: 149

```
        3       2              2       3
        I                     *        I
        I                              I
        I                              I
4               1   1                        * 4
- - -    - -        - - -            -   - -
5                 * 8   8                      5
        I                              I
        I                              I
        I   *                          I
        6       7              7       6
```

Note that:
1. Left profile does not match normal.
2. Left profile does not match right profile.
3. Left static profile does not match left stress profile, while the right static matches the right stress.
4. Excessive Contralateral Asymmetry.
5. Of special interest; the extreme difference in cooling after the stress.

CASE STUDY NO. 3

Fibrocystic

The patient presented small, dense, nodular breasts that were tender pre-menstrually. Mammography revealed no findings indicative of carcinoma, but confirmed a fibrocystic diagnosis.

With reference to FIGS. 4a and 4b, the following results are noted.

TABLE NO. 4

RISK INDEX SCORE: 53

| Static Readings Forehead Values: | | | Stress Readings Forehead Values: | | |
|---|---|---|---|---|---|
| 5.2 | 5.2 | 5.2 | 5.0 | 5.0 | 5.0 |
| | | | Cooling | | |

| | Right | CAS | Left | Right | Left | | Right | CAS | Left |
|---|---|---|---|---|---|---|---|---|---|
| N | 4.6 | .0 | 4.6 | −.2 | −.2 | N | 4.4 | .0 | 4.4 |
| 1 | 5.1 | .1 | 5.1 | −.2 | −.2 | 1 | 4.9 | .0 | 4.9 |
| 2 | 5.3 | .1 | 5.3 | −.2 | −.2 | 2 | 5.1 | .0 | 5.1 |
| 3 | 5.0 | .2 | 5.0 | −.2 | −.2 | 3 | 4.8 | .2 | 4.8 |
| 4 | 5.0 | .5 | 5.3 | −.3 | −.3 | 4 | 4.7 | .6 | 5.0 |

TABLE NO. 4-continued

| | | | | | | | | |
|---|---|---|---|---|---|---|---|---|
| 5 | 4.7 | .1 | 4.6 | −.2 | −.2 | 5 | 4.5 | .1 | 4.4 |
| 6 | 4.6 | .0 | 4.5 | −.2 | −.2 | 6 | 4.4 | .1 | 4.3 |
| 7 | 4.8 | .0 | 4.8 | −.2 | −.1 | 7 | 4.6 | .1 | 4.7 |
| 8 | 5.6 | .7 | 5.0 | −.2 | −.1 | 8 | 5.4 | .6 | 4.9 |
| Mean | | | | | | | | |
| | 5.0 | | 4.9 | −.2 | −.2 | | 4.8 | | 4.8 |

AREAS OF CONCERN ARE INDICATED BELOW
GST INDEX SCORE 53

| REFERENCE MONITOR: 187 | REFERENCE MONITOR: 149 |
|---|---|
| ```
      3    2              2    3
           I              I
           I              I
           I              I
   4           1  1                * 4
   - - -  - -    - - -        -  - -
   5           8  8                  5
           I              I
           I              I
        *  I  *           I
``` | |

Note that:
1. Both breast average values are near the forehead value.
2. Areas of concern in both breasts are indicated.
3. Mirror image hyperthermias is seen in Sector 4.
4. The profiles generally match each other.
5. The profiles are flatter than normal.
6. No major Contralateral Asymmetries as shown.

In general, the fibrocystic patient will exhibit bilateral elevations of the breast values at or above the forehead level similar to the menstruating or pregnant patient. Frequently, masses in both breasts and the breast diagram will concur. The fibrocystic profile is more "flattened" than normal and the profile level may change in response to her menstrual cycle. The normal tissue will change most and the nodular tissue will change least. Serial examinations on a weekly basis for four weeks many times will help to confirm a physician's suspicions of the fibrocystic profile.

CASE STUDY NO. 4

Malignancy, Left Breast

The patient was presented with a mass in her left breast and the physician concurred after clinical examination.

With the reference to FIGS. 5a and 5b, the following results are noted.

TABLE NO. 5

RISK INDEX SCORE: 93

| Static Readings Forehead Values: | | | Stress Readings Forehead Values: | | | | | |
|---|---|---|---|---|---|---|---|---|
| 3.9 | 3.9 | 3.9 | 3.3 | 3.6 | 3.5 | | | |
| | | | Cooling | | | | | |
| Right | CAS | Left | Right | Left | | Right | CAS | Left |
| N | 2.9 | .4 | 2.5 | −1.7 | 1.0 | N | 1.1 | 2.5 | 3.6 |
| 1 | 3.2 | .2 | 3.5 | −1.1 | .6 | 1 | 2.1 | 1.9 | 4.1 |
| 2 | 2.9 | .7 | 3.5 | −.4 | .0 | 2 | 2.5 | .1 | 3.5 |
| 3 | 2.8 | .6 | 3.2 | .4 | .7 | 3 | 3.2 | .9 | 3.9 |
| 4 | 2.6 | .7 | 3.1 | −.7 | .7 | 4 | 1.9 | 2.1 | 3.7 |
| 5 | 2.6 | .1 | 2.5 | −.8 | .8 | 5 | 1.8 | 1.8 | 3.3 |
| 6 | 2.7 | .2 | 2.8 | .0 | 1.0 | 6 | 2.7 | 1.3 | 3.8 |
| 7 | 3.5 | .5 | 3.0 | −.8 | .6 | 7 | 2.7 | .9 | 3.6 |
| 8 | 3.6 | .4 | 3.3 | −1.4 | .6 | 8 | 2.2 | 1.7 | 3.9 |
| Mean | | | | | | | | |
| | 3.0 | | 3.1 | −.6 | .6 | | 2.4 | | 3.7 |

AREA OF CONCERN ARE INDICATED BELOW
GST INDEX SCORE 93
RIGHT REFERENCE         LEFT REFERENCE

TABLE NO. 5-continued

| MONITOR: 187 | MONITOR: 149 |
|---|---|
| ```
      3    2              2    3
           I              I   *
           I              I
           I              I
   4           1  1                * 4
   - - -  - -    - - -        -  - -
   5           8  8                * 5
           I              I
           I              I
           I              I   *
        6  7              7    6
``` | |

Note that:
1. The left profile is relatively flat while right is relatively normal.
2. The left average differs from right by 1.1° C.
3. The left average is above forehead temperature.
5. Special interest: A flat profile, above forehead temperature.

CASE STUDY NO. 5

Pre-Menstrual Profile

When a patient approaches menstruation, the average temperature values of the breast elevate to a value approaching or exceeding the forehead value. The various hormone receptors of the breast respond to the changes in the hormone level of the patient, and this must be compensated for when evaluating the patient's condition.

With reference to FIGS. 6a and 6b, the following results

TABLE NO. 6

RISK INDEX SCORE: 44

| Static Readings Forehead Values: | | | | | Stress Readings Forehead Values: | | | |
|---|---|---|---|---|---|---|---|---|
| 5.5 | 5.7 | 5.8 | | | 5.5 | 5.4 | 5.5 | |
| | | | Cooling | | | | | |
| Right | CAS | Left | Right | Left | | Right | CAS | Left |
| N | 4.1 | .5 | 3.6 | .0 | −.2 | N | 4.2 | .8 | 3.4 |
| 1 | 5.5 | .1 | 5.5 | −.1 | −.4 | 1 | 5.5 | .5 | 5.1 |
| 2 | 5.4 | .2 | 5.1 | −.2 | −.3 | 2 | 5.2 | .2 | 4.8 |
| 3 | 5.2 | .2 | 5.1 | −.1 | −.4 | 3 | 5.1 | .1 | 4.7 |
| 4 | 5.0 | .3 | 5.1 | −.2 | −.3 | 4 | 4.9 | .2 | 4.7 |
| 5 | 4.8 | .3 | 5.0 | −.2 | −.4 | 5 | 4.6 | .2 | 4.6 |
| 6 | 4.8 | .3 | 5.0 | −.2 | −.3 | 6 | 4.6 | .2 | 4.7 |
| 7 | 5.2 | .2 | 5.4 | −.3 | −.4 | 7 | 4.8 | .2 | 5.0 |
| 8 | 5.8 | .3 | 5.6 | −.6 | −.4 | 8 | 5.2 | .1 | 5.2 |
| Mean | | | | | | | | |
| | 5.2 | | 5.2 | −.2 | −.4 | | 5.0 | | 4.9 |

AREAS OF CONCERN ARE INDICATED BELOW
GST INDEX SCORE 53

| REFERENCE MONITOR: 187 | REFERENCE MONITOR: 149 |
|---|---|
| ```
      3    2              2    3
           I              I
           I              I
           I              I
   4           1  1                  4
   - - -  - -    - - -        -  - -
   5           8  8                  5
           I              I
           I              I
           I              I
``` | |

Note that:
1. The profiles are flattened slightly.
2. The profiles' average values approach the forehead value.
3. The profiles are similar to the composite normal.

4. The profiles match each other.
5. The nipples of both breasts are the coldest values.
6. The cooling response is slight, but bilateral.

Experimental breast screening has been conducted, at various centers, utilizing earlier embodiments of the methodology of the present invention. In one center GST® Index Scores produced by the practice of this invention were compared to pathological findings on biopsy with respect to 315 women with symptomatic breast disease. Although women with breast cancer are more likely to have a GST® Index Score above 40, only 7% had scores below that. Such a relatively low frequency of false negatives is clinically acceptable. The results of the foregoing study are shown in the following Table 7.

TABLE 7

| Index Score | Benign | A typical | Cancer |
|---|---|---|---|
| 1-40 | 16 | 4 | 11 ( 7% of cancers) |
| 41-69 | 70 | 6 | 50 (31% of cancers) |
| 70-99 | 66 | 11 | 101 (62% of cancers) |
|  |  |  | 100% |

When data was compiled utilizing the method of the invention, there were less false positives in detecting normal tissue and less false negatives in detecting abnormal tissue than in the copending parent patent application entitled "Method for Identifying the Presence of Abnormal Tissue", Ser. No. 183,966. There was a greater than 70% accuracy in detecting the presence of cancer. (Prior methods yielded 57%-65% accuracy.)

Thus, the present invention discloses an integrated methodology for the detection of abnormal or diseased tissue which provides the combination of advantages and capabilities described above.

Other variations and applications of this invention will be apparent to persons skilled in this field without departing from the spirit and scope thereof. The present invention, therefore, is not intended to be limited to the particular method or application disclosed herein; nor is it limited to humans, females, or to any particular part of the body.

What is claimed is:

1. An objective quantitative method for identifying tissue suspected of being abnormal in at least a first portion of the body of a living organism, the method comprising the steps of:
   (a) providing means for storing data;
   (b) measuring the static temperature of at least one area of a second portion of said body by thermally responsive measurement means and storing the same in said storage means, said second portion body temperature being responsive to general temperature changes in said body and serving as a first reference temperature;
   (c) dividing said first body portion into a plurality of imaginary radial sectors extending from a central sector;
   (d) measuring the static temperatures of said first body portion at least once at a plurality of points within each of said sectors to provide a plurality of temperatures for each sector relative to said first reference temperature thereby producing a static scan over each sector of said first body portion, said measurement being taken with said measurement means;
   (e) determining a first average static temperature for each sector from the plurality of sector temperatures;
   (f) storing the plurality of average static sector temperatures and the sectors of said first body portion to which they relate in said storage means;
   (g) storing an average static temperature for said first body portion determined from said plurality of average static sector temperatures in said storage means;
   (h) correlating said first average static sector temperatures to a corresponding set of expected static sector temperatures pre-stored in said storage means, wherein said expected static sector temperatures are prior temperature measurements made of said first body portion and adjusted for physiological changes;
   (i) administering a stress to said body;
   (j) remeasuring the temperature of at least one area of said second body portion after said stress, said remeasured temperature serving as a second reference temperature;
   (k) remeasuring the temperatures of said first body portion at least once at a plurality of points within each of said sectors to provide a plurality of temperatures for each sector during said stress relative to said second reference temperature, said remeasurement being taken with thereby producing a stress scan over each sector of said first body portion, said measurement means;
   (l) determining a second average temperature for each sector from the plurality of temperatures measured during the stress scan;
   (m) storing the plurality of second average sector temperatures from said stress scan and the sectors of said first body portion to which they relate in said storage means;
   (n) storing an average temperature for said first body portion determined from said plurality of second average sector temperatures measured during said stress scan and stored in said storage means;
   (o) correlating said plurality of second average sector temperatures from said stress scan to a corresponding set of said expected static sector temperatures pre-stored in said storage means, wherein said expected static sector temperatures are prior temperature measurements made of said first body portion adjusted for physiological changes;
   (p) providing means for selectively displaying objective data;
   (q) selectively providing as output on said display means said first average static sector temperatures and said first reference temperature and said second average sector temperatures and said second reference temperature to provide a temperature topological profile of said first body portion;
   (r) determining from said temperature topological profile the probability that any of said sectors in said first body portion contains abnormal tissue.

2. The method of claim 1 wherein said stress is administered by physiologically cooling said body.

3. The method of claim 2 wherein said physiological cooling is achieved by placing at least one extremity of said body in icewater for a predetermined period of time.

4. The method of claim 3 wherein said stress scan temperature measurements are started at least ninety seconds after removal of the at least one extremity from said ice water.

5. The method of claim 1 wherein said organism is a human being, and said second body portion is the forehead thereof.

6. The method of claim 5 wherein the difference between said first reference temperature of said second body portion and said second reference temperature of said second body portion comprises a decrease in temperature occurring during an interval of one to ten minutes following said stress.

7. The method of claim 1 wherein said thermally responsive measurement means is an instrument having a detector which is sensitive to either microwave or infrared radiation.

8. The methods of claim 7 wherein said probability is determined by:
(i) measuring the difference between an average static forehead temperature and the average right breast static temperature;
(ii) measuring the difference between the average static forehead temperature and the average left breast static temperature;
(iii) providing means for summing the differences in steps i and ii together;
(v) generating a correlation parameter by correlating the average right breast temperature to a corresponding set of expected right breast temperatures prestored in said storage means, and correlating the average left breast temperature to a corresponding set of expected left breast temperatures prestored in said storage means;
(v) generating a basic parameter which provides the greatest discrimination between normal and abnormal tissue utilizing the sum from step iii and the correlation parameter;
(vi) determining the average breast temperature from said plurality of average sector temperatures for each breast and storing said average breast temperature in said storage means during said stress scan and said static scan;
(vii) measuring the difference between the average right breast temperature and the average left breast temperature for the static scan and the stress scan to provide a worst breast average asymmetry;
(viii) measuring the maximum difference between the average sector temperature of the right breast and the corresponding average temperature of its mirror image counterpart sector of the left breast corrected for expected temperatures based on statistical averages attributable to cup size differential and difference in blood flow due to cardiac proximity to provide contralateral asymmetry;
(ix) providing determining means for determining the number of breast sectors whose average stress temperature is greater than or equal to the average stress forehead temperature for each breast to provide forehead to breast sector symmetry;
(x) determining using said determining means the difference between the number of sectors for each breast whose average stress temperature is greater than or equal to the average stress forehead temperature to provide forehead to breast differential sector asymmetry;
(xi) determining the number of sectors for each breast whose average temperature is less than the nipple average temperature during the stress scan and then taking the difference between the number for each breast to compute nipple rank;
(xii) determining the amount of cooling which occurs as a result of the stress by taking the difference between the average temperature per sector during a static scan minus the average temperature per sector during the stress scan, wherein minimum cooling is the lowest value and maximum cooling is the highest value;
whereby said is determined by adding the parameters determined in steps (v) through (xii).

9. The method of claim 8 wherein said temperature measurement means comprises a detector responsive to thermal radiation, and said temperature measurements of said breasts are made by passing said detector over said sectors in a predetermined sequential order, each sector being scanned for at least five seconds.

10. The method of claim 8 having the additional steps of comparing said worst breast average asymmetry with predetermined parameters using said determining means; and
if said worst breast average asymmetry is greater than 6, subtracting 6 from said worst breast average asymmetry and multiplying the difference by 3 to provide a first number, and
if the worst breast average asymmetry is greater than 8, subtracting 8 from the worst breast average asymmetry, multiplying by 3, and adding to said first number.

11. The method of claim 8 having the additional steps of determining with said determining means, said contralateral asymmetry such that if the contralateral asymmetry is less than 7, substracting 7 from the contralateral asymmetry and multiplying by 2 to compute a first number, if the contralateral asymmetry is greater than 12, subtracting 12 from the contralateral asymmetry and multiplying by 3 to compute a second number, and if the contralateral asymmetry is greater than 15, subtracting 15 from the contralateral asymmetry, multiplying by 2, and adding to said second number.

12. The method of claim 8 having the additional step of computing a third parameter to be added to the basic parameter such that if said forehead to breast differential sector asymmetry is less than 3, multiplying said forehead to breast differential sector asymmetry by 2, and if said forehead to breast differential sector asymmetry is greater than 3, subtracting 3 from the forehead to breast differential sector asymmetry, multiplying by 3, adding to said first number.

13. The method of claim 8 having the additional steps of determining a fifth parameter such that if the nipple rank is greater than 3, subtracting 3 from the nipple rank, and multiplying by 3.

14. The method of claim 8 having the additional step of determining a fixed parameter such that if the maximum cooling is less than 4, subtracting 4 from the maximum cooling, and multiplying by four, and if the maximum cooling is greater than 8, subtracting 8 from the maximum cooling and multiplying by two.

15. The method of claim 8 having additional steps of determining a seventh parameter wherein if the minimum cooling is greater than 2, subtracting 2 from the minimum cooling and multiplying by three to provide a first number, and if the minimum cooling is greater than five, subtracting 5 from the minimum cooling and adding to said first number.

16. The method of claim 8 having the additional steps of computing said probability such that if the probability is less than 1 it is reported as 1, if greater than 80 then the result is compressed according to a logarithmic scheme, the maximum value being set as 99.

17. The method of claim 8 having the additional steps of:
(i) comparing said worst breast average asymmetry with predetermined parameters using said determining means, and if said worst breast average asymmetry is greater than 6, subtracting 6 from said worst breast average asymmetry and multiplying the difference by 3 to provide a first number, and if the worst breast average asymmetry is greater than 8, subracting 8 from the worst breast average asymmetry, multiplying by 3, and adding to said first number;
(ii) determining with said determining means said contralateral asymmetry such that if the contralateral asymmetry is less than 7, subtracting 7 from the contralateral asymmetry and multiplying by 2 to compute a first number, if the contralateral asymmetry is greater than 12, subtracting 12 from the contralateral asymmetry and multiplying by 3 to compute a second number, and if the contralateral asymmetry is greater than 15, subtracting 15 from the contralateral asymmetry, multiplying by 2, and adding to said second number;
(iii) computing a third parameter to be added to the basic parameter such that if said forehead to breast differential sector asymmetry is less than 3, multiplying said forehead to breast differential sector asymmetry by 2, and if said forehead to breast differential sector asymmetry is greater than 3, subtracting 3 from the forehead to breast differential sector asymmetry, multiplying by 3, adding to said first number; and
(iv) determining a fifth parameter such that if the nipple rank is greater than 3, subtracting 3 from the nipple rank and multiplying by 3;

adding the parameters of steps (i), (ii), (iii), and (iv) to said basic parameter to compute a raw probability such that if the raw probability is greater than 80, the probability will be determined by subtracting 80 from said raw probability, dividing by 25, adding 80, and taking the square root of the difference between the raw score and 80, and if the raw score is greater than 99, then the probability will equal 99.

18. The method of claim 1 wherein said organism is a human being, said first body portion comprising the left and right breasts of said body, each of which is imaginarily divided into eight radial sectors with the nipple thereof constituting a separate centrally disposed sector, and said temperature measurements are made of said radial sectors in a predetermined sequence.

19. The method of claim 18 wherein said average temperatures for the central sector nipple, the forehead, and each and every radial sector, comprises every combination of four consecutive data points within each area which are averaged together such that the highest running four point data average is considered to be the average temperature of the sector, nipple, or forehead.

20. The method of claim 1 having the additional step of providing a microprocessor means and an operator for detecting errors in the input and output of data by:
(i) converting the analog temperature data to digital form;
(ii) storing the measured data in digital form;
(iii) selecting the most representative data;
(iv) storing the selected data in electronic memory and displaying it on a video screen;
(v) checking the video screen by the operator to observe whether any pertinent measurements are incomplete, out of sequence, unrecorded or clearly erroneous, such that the operator will become alerted to the non-standard performance;
(vi) correcting the error.

* * * * *

UNITED STATES PATENT AND TRADEMARK OFFICE
CERTIFICATE OF CORRECTION

PATENT NO. : 4,428,382

DATED : Jan. 31, 1984

INVENTOR(S) : Walsall et al.

It is certified that error appears in the above-identified patent and that said Letters Patent is hereby corrected as shown below:

| COLUMN | LINE | |
|--------|------|---|
| 13 | 3 | Delete "CST", insert -- GST -- |

Signed and Sealed this

Sixth Day of August 1985

[SEAL]

Attest:

DONALD J. QUIGG

*Attesting Officer*     *Acting Commissioner of Patents and Trademarks*